United States Patent
Huang et al.

(10) Patent No.: US 8,779,014 B2
(45) Date of Patent: Jul. 15, 2014

(54) SLURRY CATALYST AND THE PREPARATION THEREOF

(75) Inventors: Wei Huang, Taiyuan (CN); Zhihua Gao, Taiyuan (CN); Lihua Yin, Taiyuan (CN); Kechang Xie, Taiyuan (CN)

(73) Assignee: Taiyuan University of Technology (CN)

( * ) Notice: Subject to any disclaimer, the term of this patent is extended or adjusted under 35 U.S.C. 154(b) by 724 days.

(21) Appl. No.: 12/518,121

(22) PCT Filed: Oct. 25, 2007

(86) PCT No.: PCT/CN2007/003039
§ 371 (c)(1),
(2), (4) Date: Jun. 8, 2009

(87) PCT Pub. No.: WO2008/071059
PCT Pub. Date: Jun. 19, 2008

(65) Prior Publication Data
US 2010/0010271 A1    Jan. 14, 2010

(30) Foreign Application Priority Data
Dec. 14, 2006   (CN) .......................... 2006 1 0102268

(51) Int. Cl.
*B01J 23/80* (2006.01)
*C07C 27/00* (2006.01)

(52) U.S. Cl.
USPC ........... 518/713; 518/714; 518/715; 502/302; 502/307; 502/324; 502/342

(58) Field of Classification Search
CPC ...................................................... C07C 41/01
USPC .......... 568/713, 714, 715; 502/302, 307, 324, 502/342
See application file for complete search history.

(56) References Cited

U.S. PATENT DOCUMENTS

| | | | |
|---|---|---|---|
| 5,254,520 A | 10/1993 | Sofianos | |
| 5,908,963 A | 6/1999 | Voss et al. | |
| 6,147,125 A | 11/2000 | Shikada et al. | |
| 6,562,306 B1 | 5/2003 | Shikada et al. | |
| 6,696,388 B2 * | 2/2004 | Kourtakis et al. | ............. 502/320 |
| 6,800,665 B1 | 10/2004 | Shikada et al. | |
| 7,033,972 B2 | 4/2006 | Shikada et al. | |
| 2006/0052647 A1 | 3/2006 | Shikada et al. | |

FOREIGN PATENT DOCUMENTS

| | | | | |
|---|---|---|---|---|
| CN | 1173393 A | | 2/1998 | |
| CN | 1043409 C | | 5/1999 | |
| CN | 1043739 C | | 6/1999 | |
| CN | 1338332 A | | 3/2002 | |
| CN | 1085647 C | | 5/2002 | |
| CN | 1131108 C | | 12/2003 | |
| CN | 1139427 C | | 2/2004 | |
| CN | 1169618 C | | 10/2004 | |
| CN | 1202061 C | | 5/2005 | |
| CN | 1613560 | * | 5/2005 | .............. B01J 37/03 |
| CN | 1613560 A | | 5/2005 | |
| CN | 1247506 C | | 3/2006 | |

OTHER PUBLICATIONS

Human assisted Machine Translation to English of CN 1613560(A), published May 2005.*

* cited by examiner

*Primary Examiner* — Rosalynd Keys
(74) *Attorney, Agent, or Firm* — Drinker Biddle & Reath LLP

(57) ABSTRACT

The present invention provides a slurry catalyst and a method for preparing the same, and belongs to the technical field of preparing catalyst. Particularly, the present invention provides a slurry catalyst directly used in a slurry bed reactor for synthesizing methanol and dimethyl ether and a method for preparing the same, which uses the complete liquid phase preparation from solution to slurry without the conventional slurry-producing process of firstly forming a solid catalyst and dispersing it into an inert medium after crushing and milling. This catalyst mainly comprises Cu, Zn, Al and Zr, wherein atomic ratios of each of components are Cu/Zn/(Al+Zr)=1/0.1-5/0.15-15 and Zr/Al=1:1.0-1:30, and one or two selected from the group consisting of lanthanide metals, Mn, Mo, Si, V, W, Cr, Mg, Ni, K, Pd, Rh, Ru, Re, Pt and Sr is used a promoter. The catalyst prepared in the present invention has the advantages of good stability, high selectivity of alcohol and ether, good rheological behavior and strong wear resistance.

7 Claims, No Drawings

SLURRY CATALYST AND THE PREPARATION THEREOF

CROSS-REFERENCE TO RELATED APPLICATIONS

This application is a national stage application (under 35 U.S.C. §371) of PCT/CN2007/003039, filed Oct. 25, 2007, which claims benefit of Chinese application 200610102268.1, filed Dec. 14, 2006.

FIELD OF THE INVENTION

The present invention relates to a slurry catalyst and a method for preparing the same, and belongs to the technical field of preparing catalyst. Specifically, the present invention relates to a slurry catalyst directly used in a slurry bed reactor for directly synthesizing methanol and dimethyl ether from syngas, and a method for preparing the same, which is also suitable for various slurry bed reactors to prepare catalysts.

BACKGROUND OF THE INVENTION

The energy source structure of our country is rich in coal but poor in natural gas or petroleum. With the continued progress of social economy and increasing improvement of people's living standard, the demand of energy source is daily on the increase, especially in the field of cleaning civil fuel and vehicle fuel, the increasing rate is much faster. Therefore, to base ourselves upon China and vigorously develop coal-based synthetic liquid alternative fuels will be one of the important routes to address the problem of the safe supply of energy sources. Compared to other coal-based fuels, coal-based oxygenated fuels, i.e., methanol fuels and dimethyl ether fuels, not only possess remarkable advantages of technique and economy, but also make full utilization of the three elements of C, H, O in coals, which can achieve the sustainable development of the resources, energy sources, environment and economy.

In recent years, much attention is paid to slurry bed reactors due to their advantages of favourable heat transfer, easy of temperature constant operation, and especially suitability for the poly-generation process of heat, electrical and chemical products. Slurry bed reactors are one of the most advanced reactors for producing alcohols and ethers which are currently researched and developed. However, the stability of catalyst is a main factor influencing the normal operation of the synthesis of alcohols and ethers in a slurry bed reactor, thus how to enhance the stability of catalyst is becoming the focus of research. Currently, many of patents in this field focus on the selection of process conditions, the reconstruction of reactors, and the improvement of catalysts, for example, CN131108C, CN1139427C, CN1043739C, CN1043409C, CN1169618C, CN1172893C, CN1039224C, CN1085647C, CN1202061C, CN1247506C, etc., while there is little report on the technique for producing a catalyst specific for the use characteristics of slurry bed reactors. By far, most catalysts used in slurry bed reactors are produced by firstly forming a solid catalyst, crushing and milling it, and then dispersing it into an inert medium to produce a slurry. Only Chinese Patent Application No. 200410012537.6 owned by ourselves discloses a slurry catalyst having similar phase structure and pore structure of a solid catalyst and formed directly from raw materials, as well as its preparation method. The method comprises firstly preparing a gel containing a catalyst comprised of CuZnAl, CuZr and CuTi, soaking thus obtained gel in an organic solvent such as an alcohol, a ketone, an ester, or the like, then dispersing the soaked gel into an organic medium, and then heat treating it at an atmosphere of mixed $N_2$ and $O_2$ within a certain temperature range. Further study reveals that when the catalysts of CuZnAl and CuZr are used in a slurry bed reactor to synthesize methanol and dimethyl ether, the catalyst CuZnAl has good activity but poor rheological behavior and wear resistance whilst the catalyst CuZr has good rheological behavior and wear resistance but poor activity. Furthermore, it is found that both the gel surface treatment process involved during preparation of the catalyst for a slurry bed reactor and the heat treatment atmosphere of the gel dispersion have significant effect on the properties of the catalyst.

DESCRIPTION OF THE INVENTION

The slurry catalyst and the method for preparing the same of the present invention are aimed at providing a slurry catalyst having good activity, stability, rheological behavior and wear resistance and directly used in a slurry bed reactor for synthesizing methanol and dimethyl ether as well as a method for preparing the same based on the patents described above by extending the surface treatment process and the heat treatment atmosphere of the gel dispersion during preparation of the catalyst and combining respective advantages of CuZnAl and CuZr catalysts.

The slurry catalyst of the present invention is a catalyst for a slurry bed reactor, which is characterized by being a catalyst directly used in a slurry bed reactor for synthesizing methanol and dimethyl ether, the composition of which being characterized as the general formula of CuZnMZrAl, wherein the atomic ratios of each of components are as follows: Cu/Zn/(Al+Zr)=1/0.1-5/0.15-15 and Zr/Al=1:1.0-1:30, and M is a promoter which is one or two selected from the group consisting of lanthanide metals, Mn, Mo, Si, V, W, Cr, Mg, Ni, K, Pd, Rh, Ru, Re, Pt and Sr, and M:Cu is 0-0.5.

The method for preparing the slurry catalyst as above is characterized by being a method for preparing a slurry catalyst used in a slurry bed for synthesizing methanol and dimethyl ether, the method comprising the steps of:

I. using aluminum isopropoxide, zirconium oxynitrate, cupric nitrate and zinc nitrate as raw materials to prepare a gel A containing CuZnMZrAl component by way of combination-multistep feeding, wherein the promoter M is added together with cupric nitrate;

II. after stewing and aging, the gel A being subjected to azeotropic distillation treatment to prepare a gel B;

III. dispersing homogeneously the gel B in an organic medium in the presence of a surfactant to prepare a gel dispersion C; and IV. treating the gel dispersion C in a reaction kettle with an inter gas, an oxidative gas, a reductive gas or a mixed gas thereof in any combination thereof for 2-72 hours under programmed temperature ranging from room temperature to 673K and at a heating rate of from 0.5K/mm to 20K/min to prepare the slurry catalyst.

The combination-multistep feeding as described above means feeding aluminum isopropoxide, zirconium oxynitrate, cupric nitrate and zinc nitrate in a sequential way of any combination thereof in two, three or four steps.

The solvent used in the solvent substitution as described above is an organic solvent such as a alcohol, a ketone, an ester, siloxane or a silane compound.

The azeotropic agent used in the azeotropic distillation as described above is a hydrocarbon, an oxygen-containing organic compound or a nitrogen-containing organic compound.

The surfactant as described above is an ionic, non-ionic or amphoteric surfactant, and the addition amount thereof is 0.1~10%.

The inert gas as described above is $N_2$, Ar or He. The oxidative gas is $O_2$, $CO_2$ or nitrogen oxides. The reductive gas is CO, $H_2$, $CH_4$, lower hydrocarbons or a mixture of lower hydrocarbons.

The advantages of the slurry catalyst and the method for preparing the same of the present invention are that the catalyst will not deactivate after working for 1000 hours, and has good stability, high selectivity of alcohols and ethers, low viscosity, good rheological behavior, and strong wear resistance in that the particle size and shape of the catalyst remain the same after and before reaction.

The method for preparing the slurry catalyst of the present invention is also suitable for preparing the catalysts used in various slurry bed reactors.

EXAMPLES

The catalyst and the method for preparing the same of the present invention are further illustrated below with reference to the following Examples.

Example 1

27.54 g of aluminum isopropoxide and 15.30 g of zirconium oxynitrate are dissolved in 290 ml of deionized water, and the resultant is refluxed under stirring for 3.5 hours at 353K. Then, 32.75 g of cupric nitrate and 19.83 g of zinc nitrate are dissolved in 50 ml of deionized water, and the resultant is added into the above sol. The resultant is heated and stirred until a gel is formed. After stewing and aging for 15 days, the gel is substituted by acetone three times within 24 hours, and the supernatant is decanted, and then 160 ml of liquid paraffin and 1 ml of Span 80 are added and dispersed to form a homogeneous and stable gel dispersion. The gel dispersion is charged into a reaction kettle, heated under the action of 100% $N_2$ from room temperature to 553K at a heating rate of 1K/min and treated for 16 hours to obtain a slurry catalyst.

Example 2

The same procedure as in Example 1 is followed except that 27.54 g of aluminum isopropoxide is added into 190 ml of distilled water, the resultant is refluxed under stirring for 5.0 hours at 343K, and then 15.30 g aqueous zirconium oxynitrate solution is added, stirring is continued for 1.5 hours, finally 32.75 g of aqueous cupric nitrate solution and 19.83 g of aqueous zinc nitrate solution are added, and the resultant is heated and stirred until a gel is formed.

Example 3

The same procedure as in Example 1 is followed except that 27.54 g of aluminum isopropoxide is added into 190 ml of distilled water, the resultant is refluxed under stirring for 10.0 hours at 363K, and then 15.30 g of aqueous zirconium oxynitrate solution, 32.75 g of aqueous cupric nitrate solution and 19.83 g of aqueous zinc nitrate solution are added, and the resultant is heated and stirred until a gel is formed.

Example 4

The same procedure as in Example 1 is followed except that 27.54 g of aluminum isopropoxide is added into 190 ml of distilled water, the resultant is refluxed under stirring for 2.0 hours at 353K, and then 15.30 g of aqueous zirconium oxynitrate solution is added, stirring is continued for 3.0 hours, and then 32.75 g of aqueous cupric nitrate solution is added and stirred for 0.5 hours, finally 19.83 g of aqueous zinc nitrate solution is added, and the resultant is heated and stirred until a gel is formed.

Examples 5 to 7

The essentially same procedure as in Example 1 is followed except that ethanol, n-heptane and dimethyl siloxane are selected as the solvents in the solvent substitution respectively.

Example 8

48.97 g of aluminum isopropoxide and 3.40 g of zirconium oxynitrate are dissolved in 290 ml of deionized water, the resultant is refluxed under stirring for 1.0 hours at 353K. Then, 27.18 g of cupric nitrate and 33.05 g of zinc nitrate are dissolved into 50 ml of deionized water and the resultant is added into the above sol. The resultant is heated and stirred until a gel is formed. After stewing and aging for 15 days, the gel is mixed with n-butanol, then 160 ml of liquid paraffin and 1.5 ml of polyvinyl alcohol are added. The resultant mixture is mixed sufficiently, and then subjected to azeotropic distillation treatment so that water in the gel can be removed in the form of azeotrope. After water molecules are completely removed from the gel, then the gel is heated to the temperature above the boiling point of n-butanol to evaporate n-butanol. The obtained slurry is charged into a reaction kettle, heated under the action of 100% $N_2$ from room temperature to 573K at a heating rate of 20K/min and treated for 72 hours to obtain a slurry catalyst.

Examples 9 to 13

The essentially same procedure as in Example 8 is followed except that xylene, isopentanol, ethyl acetate, formic acid and pyridine are selected as azeotropic agents respectively.

Examples 14 to 20

The preparing methods of Examples 14 to 20 are essentially the same as in Example 1, wherein the composition of the gases used for programmed temperature treatment in the reaction kettle are sequentially 100% Ar, 50% $CO_2$+50% Ar, 20% $O_2$+80% $N_2$, 20% NOx+80% $N_2$, 25% $CH_4$+75% He, 30% $H_2$+70% $N_2$, 20% CO+10% $CO_2$+70% $N_2$.

Example 21

36.72 g of aluminum isopropoxide and 10.20 g of zirconium oxynitrate are dissolved in 240 ml of deionized water, and the resultant is refluxed under stirring for 10 hours at 363K. Then, 39.14 g of cupric nitrate, 11.90 g of zinc nitrate, 5.0 g of manganese nitrate and 2.4 g of lanthanum nitrate are dissolved in 50 ml of deionized water, and the resultant is added into the above sol. The resultant is heated and stirred until a gel is formed. After stewing and aging for 15 days, the gel is treated similarly with Example 1, wherein 2.5 ml of betaine is used as the surfactant.

Example 22

14.56 g of aluminum isopropoxide and 38.10 g of zirconium oxynitrate are dissolved in 290 ml of deionized water, and the resultant is refluxed under stirring for 10 hours at 343K. Then, 14.68 g of cupric nitrate, 41.65 g of zinc nitrate and 0.18 g of potassium carbonate are dissolved in 70 ml of deionized water, and the resultant is added into the above sol. The resultant is heated and stirred until a gel is formed. After stewing and aging for 15 days, the gel is treated similarly with Example 1, wherein 0.5 ml of sodium monotetradecyl phthalate is used as the surfactant.

The activity test of slurry catalysts prepared in Examples 1 to 22 is carried out in a self-made slurry bed evaluation device under the following conditions: the slurry catalysts treated in the reaction kettle is heated from room temperature to 563K at a heating rate of 5K/min in the presence of a mixed gas containing 20% $H_2/N_2$ at atmospheric pressure, kept at 563K for 10 hours, and then connected to syngas to react under the conditions that the ratio of $H_2/CO$ in the syngas is 0.2~20 by volume, the reaction pressure is 1.0~6.0 MPa and the reaction temperature is 473~593K.

TABLE 1

The results of each of Examples

| Ex. No. | Pressure (MPa) | Temperature (K) | $H_2/CO$ | CO conversion rate (C-mol %) | DME selectivity (C-mol %) | $CH_3OH$ selectivity (C-mol %) |
|---|---|---|---|---|---|---|
| 1 | 4.0 | 553 | 1/1 | 14.36 | 91.56 | 6.22 |
| 2 | 4.0 | 553 | 1/1 | 14.06 | 89.91 | 6.57 |
| 3 | 4.0 | 553 | 1/1 | 6.40 | 86.08 | 8.15 |
| 4 | 4.0 | 553 | 1/1 | 23.67 | 94.21 | 4.73 |
| 5 | 4.0 | 553 | 1/1 | 7.64 | 82.15 | 9.17 |
| 6 | 4.0 | 553 | 1/1 | 18.69 | 93.65 | 3.77 |
| 7 | 4.0 | 553 | 1/1 | 25.37 | 84.72 | 9.49 |
| 8 | 1.0 | 553 | 1/1 | 1.54 | 89.54 | 4.32 |
| 8 | 4.0 | 473 | 1/1 | 0.70 | 49.99 | 35.53 |
| 8 | 4.0 | 493 | 1/1 | 1.15 | 55.26 | 30.25 |
| 8 | 4.0 | 513 | 1/1 | 3.35 | 70.54 | 21.51 |
| 8 | 4.0 | 533 | 1/1 | 8.53 | 85.03 | 10.00 |
| 8 | 4.0 | 553 | 1/1 | 14.18 | 90.95 | 4.45 |
| 8 | 4.0 | 573 | 1/1 | 11.24 | 89.64 | 5.61 |
| 8 | 4.0 | 593 | 1/1 | 10.96 | 89.71 | 5.54 |
| 8 | 6.0 | 593 | 1/1 | 21.56 | 91.02 | 4.69 |
| 8 | 4.0 | 553 | 1/5 | 5.55 | 84.41 | 10.81 |
| 8 | 4.0 | 553 | 1/3 | 7.16 | 87.76 | 7.52 |
| 8 | 4.0 | 553 | 1/2 | 9.29 | 89.75 | 4.96 |
| 8 | 4.0 | 553 | 2/3 | 10.74 | 90.81 | 4.45 |
| 8 | 4.0 | 553 | 3/1 | 31.27 | 87.48 | 7.27 |
| 8 | 4.0 | 553 | 5/1 | 36.89 | 85.54 | 9.15 |
| 8 | 4.0 | 553 | 10/1 | 18.51 | 55.95 | 30.82 |
| 8 | 4.0 | 553 | 20/1 | 12.73 | 31.33 | 45.69 |
| 9 | 4.0 | 553 | 1/1 | 20.61 | 88.23 | 6.76 |
| 10 | 4.0 | 553 | 1/1 | 11.31 | 65.91 | 20.68 |
| 10 | 4.0 | 553 | 1/1 | 25.67 | 90.12 | 7.84 |
| 12 | 4.0 | 553 | 1/1 | 12.59 | 53.84 | 39.61 |
| 13 | 4.0 | 553 | 1/1 | 19.81 | 77.63 | 18.37 |
| 14 | 4.0 | 553 | 1/1 | 12.38 | 89.39 | 2.93 |
| 15 | 4.0 | 553 | 1/1 | 15.79 | 92.25 | 2.98 |
| 16 | 4.0 | 553 | 1/1 | 10.37 | 88.74 | 1.57 |
| 17 | 4.0 | 553 | 1/1 | 9.64 | 81.61 | 9.45 |
| 18 | 4.0 | 553 | 1/1 | 7.54 | 82.36 | 6.45 |
| 19 | 4.0 | 553 | 1/1 | 14.61 | 65.76 | 29.84 |
| 20 | 4.0 | 553 | 1/1 | 18.63 | 85.19 | 7.66 |
| 21 | 4.0 | 553 | 1/1 | 30.15 | 87.64 | 10.55 |
| 22 | 4.0 | 553 | 1/1 | 20.45 | 80.24 | 16.93 |

Many modifications and alterations of the catalyst and process of making the catalyst of this invention may be made without departing from the scope of this invention which is limited only by the claims.

The invention claimed is:

1. A method for preparing a slurry catalyst according to a composition of a general formula of CuZnMZrAl, wherein the atomic ratios of each of components are as follows: Cu/Zn/(Al+Zr)=1/0.1-5/0.15-15 and Zr/Al=1:1.0-1:30, and M is a promoter which is one or two selected from the group consisting of lanthanide metals, Mn, Mo, Si, V, W, Cr, Mg, Ni, K, Pd, Rh, Ru, Re, Pt and Sr, and M:Cu is 0-0.5, for synthesizing methanol and dimethyl ether in a slurry bed reactor which comprises:

I. mixing aluminum isopropoxide, zirconium oxynitrate, cupric nitrate and zinc nitrate as raw materials to prepare a gel A containing CuZnMZrAl components by way of a combination-multistep feeding, wherein a promoter M is added together with cupric nitrate;

II. after stewing and aging, gel A is subjected to azeotropic distillation treatment to prepare gel B;

III. dispersing homogeneously gel B in an organic medium in the presence of a surfactant to prepare gel dispersion C; and IV. treating gel dispersion C in a reaction kettle with 100% inert gas for 2-72 hours under programmed temperature ranging from room temperature to 673K and at a heating rate of from 0.5K/min to 20K/min to prepare the slurry catalyst.

2. The method of claim 1 for preparing a slurry catalyst wherein said combination-multistep feeding comprises feeding aluminum isopropoxide, zirconium oxynitrate, cupric nitrate and zinc nitrate in a sequential way of any combination thereof in two, three or four steps.

3. The method of claim 1 for preparing a slurry catalyst wherein the azeotropic agent in said azeotropic distillation is an oxygen-containing organic compound or a nitrogen-containing organic compound.

4. The method of claim 1 for preparing a slurry catalyst wherein said surfactant is an ionic, non-ionic or amphoteric surfactant, and the addition amount thereof is 0.1 to about 10%.

5. The method of claim 1 for preparing a slurry catalyst wherein said inert gas comprises $N_2$, Ar, or He.

6. A method for preparing a slurry catalyst according to the general formula of CuZnMZrAl, wherein the atomic ratios of each of components are as follows: Cu/Zn/(Al+Zr)=1/0.1-5/0.15-15 and Zr/Al=1:1.0-1:30, and M is a promoter which is one or two selected from the group consisting of lanthanide metals, Mn, Mo, Si, V, W, Cr, Mg, Ni, K, Pd, Rh, Ru, Re, Pt and Sr, and M:Cu is 0-0.5, wherein said slurry catalyst is prepared in the liquid phase without isolating or re-dispersing a solid catalyst which comprises:

I. admixing aluminum isopropoxide, zirconium oxynitrate, cupric nitrate, and zinc nitrate as raw materials by way of a combination multi-step feeding, and a promoter M selected from the group consisting of lanthanide metals, Mn, Mo, Si, V, W, Cr, Mg, Ni, K, Pd, Rh, Ru, Re, Pt, Sr where M:Cu is 0 to 0.5 is added together with cupric nitrate thereby preparing gel A;

II. stewing and aging gel A and then subjecting gel A to azeotropic distillation to prepare gel B;

III. dispersing gel B in an organic medium in the presence of a surfactant to prepare gel C;

IV. treating gel C with 100% inert gas for 2-72 hours under a programmed temperature from room temperature to 673 K at a heating rate of from 0.5k/min. to 20K/min to provide a slurry catalyst.

7. The method of claim 6 wherein a provided slurry catalyst is contacted with syngas in a slurry bed reactor to produce methanol and dimethyl ether.

* * * * *